United States Patent [19]
Hill et al.

[11] Patent Number: 5,637,231
[45] Date of Patent: Jun. 10, 1997

[54] METHOD AND APPARATUS FOR USING OZONE IN A PRESSURE VESSEL TO TREAT STREAM OF POLLUTANTS

[75] Inventors: David J. Hill, Lincoln Park; Frederick J. Hoitash, Ypsilanti, both of Mich.

[73] Assignee: Huron Valley Technology, Inc., Romulus, Mich.

[21] Appl. No.: 480,314

[22] Filed: Jun. 7, 1995

[51] Int. Cl.$^6$ .................................................. C02F 1/78
[52] U.S. Cl. .......................... 210/748; 210/760; 210/205; 210/218; 210/220; 210/252; 210/254; 261/113; 261/123; 261/124; 261/DIG. 42; 422/194; 422/220; 422/231; 422/257
[58] Field of Search ........................ 210/748, 760, 210/205, 218, 220, 252, 259; 261/113, 123, 124, DIG. 42; 422/194, 220, 231, 257

[56] References Cited

U.S. PATENT DOCUMENTS

| | | |
|---|---|---|
| 3,772,188 | 11/1973 | Edwards . |
| 4,229,202 | 10/1980 | Mullerheim et al. . |
| 4,289,594 | 9/1981 | Alpaugh et al. . |
| 4,512,900 | 4/1985 | Macur et al. . |
| 4,792,407 | 12/1988 | Zeff et al. . |
| 4,834,836 | 5/1989 | Wemhoff . |
| 4,849,114 | 7/1989 | Zeff et al. . |
| 5,043,079 | 8/1991 | Hallett . |
| 5,122,165 | 6/1992 | Wang et al. . |
| 5,126,111 | 6/1992 | Al-Ekabi et al. . |
| 5,178,755 | 1/1993 | LaCrosse . |
| 5,180,499 | 1/1993 | Hinson et al. . |
| 5,186,907 | 2/1993 | Yanagi et al. . |
| 5,190,659 | 3/1993 | Wang et al. . |
| 5,234,606 | 8/1993 | Kazama et al. . |
| 5,236,602 | 8/1993 | Jackson . |
| 5,302,298 | 4/1994 | Leitzke . |
| 5,308,480 | 5/1994 | Hinson et al. . |
| 5,374,356 | 12/1994 | Miller et al. . |

OTHER PUBLICATIONS

*McGraw–Hill Encyclopedia of Science & Technology*, 1987, vol. 16, pp. 295–297 and 302–305.
*McGraw–Hill Encyclopedia of Science & Technology*, 1987, vol. 19, pp. 323–329 and 334–336.

*Primary Examiner*—Neil McCarthy
*Attorney, Agent, or Firm*—Harness, Dickey & Pierce, P.L.C.

[57] ABSTRACT

A photocatalytic oxidation and ozone catalyst system utilizes ultraviolet light and ozone in the treatment of waste and wastewater to destroy pathogens and to break down most hydrocarbons and other chemicals into non-hazardous forms. The wastewater enters the system for initial treatment and is also pumped through the venturi loop and is exposed to ultraviolet light. The ozone interacts at the venturi before the ultraviolet light is being used as a catalyst by the ultraviolet light to break apart the double bonds of ketones, aldehydes, esters, and carboxylic acids. Following initial treatment, the wastewater is pumped into the pressurized ozone enhancement vessel where vapor oxidation of the polluting chemicals occurs. The enhancement vessel comprises a liquid spray component and a series of ozone resonator plates having ozone distribution manifolds that spray the wastewater with ozone. The plates have angular channels formed therein through which the wastewater passes. The channels are formed to maximize absorption of the ozone by the wastewater which exits the vessel in a treated form.

10 Claims, 4 Drawing Sheets

METHOD AND APPARATUS FOR USING OZONE IN A PRESSURE VESSEL TO TREAT STREAM OF POLLUTANTS

BACKGROUND OF THE INVENTION

1. Field of the Invention

The present invention relates to the treatment of waste and wastewater. More particularly, the present invention relates to a method and apparatus for using ozone in a pressure vessel to treat polluted waste and wastewater.

2. Description of the Relevant Art

The introduction of organic and inorganic substances into water supplies results in the pollution of the water are a part of the modern world. Pathogens may also be introduced into the water supply. Many of these additions to the water supply are the result of human activity, including agricultural development and industrial production, as well as the output of human communities. In some cities, approximately 200 gallons of wastewater per person are produced. This wastewater, including waste from household, agricultural, and industrial sources, is generally referred to as domestic sewage. At a certain point these additives stress the water supply to dangerous levels and require treatment and eradication.

Several methods have been developed to treat wastewater to prepare it for its return to the general water supply. Early attempts at wastewater treatment were directed to mechanical methods of sedimentation and enhancing exposure to oxygen and sunlight. The methods used today for wastewater treatment include primary treatment (passing the wastewater through screens to remove coarse elements and allowing the water to stand in tanks so that the remaining solid matter settles out) and secondary treatment (directed to the oxidization of organic matter and the removal of inorganic material and the neutralization of any bacteria and viruses that might be present in the wastewater). Secondary treatment includes the substeps of initial treatment (oxidation in oxidation ponds or filtration through crushed stone or gravel [or filters or disks] and the use of microorganisms to break down the organic and inorganic matter) and the processing of the remaining solids and liquids through the use of a settling tank and a unit for anaerobic digestion. (The outflow is directed into the settling tank to allow for settlement. Once separated, the liquid portion receives further treatment before being released into the environment, while the organic matter of the sludge is treated for stabilization using an digester.)

While being generally suitable for most forms of wastewater, these procedures fail to satisfactorily treat wastewater that is both chemically and biologically hazardous. Industrially produced chemicals such as chlorinated hydrocarbons (either aliphatic or aromatic) commonly enter wastewater. Other chemicals frequently produced at the industrial level include trichloroethylene, cyanide (from metal plating), sugars (from confectionery production), various fats, oils, and grease (from restaurants, auto facilities, and refineries), products from the plating industries, such as copper, cadmium, zinc, manganese, lead, ferrous iron, silver, and surfactants from soaps and detergents. Most of these chemicals are not biodegradable and are difficult to render nontoxic. In addition, bacterial and viral pathogens are frequently found in wastewater. Filtration and chemical treatment have only limited effect on these pollutants.

As an alternative to mechanical methods of treating such industrial wastewater, ultraviolet light has been applied to assist in the breakdown of organic waste through oxidation. Ozone ($O_3$) absorbs such light and releases oxygen atoms. These atoms react with water and result in the formation of OH radicals which are excellent oxidants. Ultraviolet light and ozone in combination with the reaction of OH radicals effects both chemical and pathogenic neutralization.

Several patents are directed to the treatment of wastewater using ultraviolet light in conjunction with an oxidizing agent. Examples of these patents include: U.S. Pat. No. 5,308,480, issued May 3, 1994, to Hinson et al. for APPARATUS FOR REMOVAL OF SOLID, CHEMICAL AND BACTERIAL WASTE FROM WATER; U.S. Pat. No. 5,302,298, issued Apr. 12, 1994, to Leitzke for PROCESS AND INSTALLATION FOR TREATING LIQUIDS CHARGED WITH POLLUTANTS; U.S. Pat. No. 5,234,606, issued Aug. 10, 1993, to Kazama et al. for METHOD AND SYSTEM FOR RECOVERING WASTEWATER; and U.S. Pat. No. 5,178,755, issued Jan. 12, 1993, to LaCrosse for UV-ENHANCED OZONE WASTEWATER TREATMENT SYSTEM.

While representing improvements in the treatment of wastewater, known systems for the treatment of chemically and pathologically polluted water fail to provide a system to efficiently, quickly, and inexpensively remove such pollutants. Accordingly, such a system is wanting in the treatment of waste and wastewater.

SUMMARY OF THE INVENTION

It is therefore an object of the present invention to overcome the disadvantages of known methods of treating flowable waste and wastewater by providing a method and apparatus for efficiently, quickly, and inexpensively removing chemical and pathological pollutants from wastewater.

It is a further object of the present invention to provide such a method and apparatus that is relatively inexpensive to construct, purchase, and to operate.

Yet a further object of the present invention is to provide such a method and apparatus that utilizes ultraviolet light and ozone to break down most hydrocarbons of hazardous waste into non-hazardous form.

Still a further object of the present invention is to provide such a method and apparatus which uses ultraviolet light to catalyze the ozone to break apart the double bonds of ketones, aldehydes, esters, and carboxylic acids.

Yet a further object of the present invention is to provide such a method and apparatus which reduces ozone to oxygen for safe release into the environment.

Still a further object of the present invention is to provide such a system which is able to meet the output flow rates of a commercial facility.

An additional object of the present invention is to provide such a method and apparatus which includes an ozone enhancement vessel for maximizing the water-treating effects of ozone.

Yet still another object of the present invention is to provide such a method and apparatus which incorporates into the ozone enhancement vessel a plurality of ozone resonator plates having upper and lower ozone distribution manifolds fitted thereto.

A further object of the present invention is to provide such a method and apparatus in which the ozone resonator plates which maximizes ozone impact on the water being treated.

The present invention comprises a photocatalytic oxidation and ozone catalyst system for treating flowable waste. A precipitate is formed with the metals filtered from the flowable waste, while organic components are oxidized and are filterable with carbon filters as required or, alternatively, through anionic and cationic filters for collection.

The system utilizes ultraviolet light at 185 nm wavelength to break down most hydrocarbons of hazardous wastewater into non-hazardous form. Ozone is produced from commercial grade oxygen and is pumped through a venturi and into a pressurized ozone enhancement vessel. (As an alternative, clean dry air passed through an air dryer could be substituted for pure oxygen.) The flowable waste enters the system for initial treatment and is also pumped through the venturi loop and is exposed to ultraviolet light. The ozone interacts at the venturi before the ultraviolet light is being used as a catalyst by the ultraviolet light to break apart the double bonds of ketones, aldehydes, esters, and carboxylic acids.

Following this initial treatment, the provisionally treated waste or wastewater is pumped into the pressurized ozone enhancement vessel where vapor oxidation of the polluting chemicals occurs. The enhancement vessel comprises a liquid spray component and a series of resonator plates, preferably between three and six of which are provided. One or more drip plates having angled channels defined therein are optionally provided.

The provisionally treated waste or wastewater enters the top of the enhancement vessel and passes through a nozzle onto the uppermost or first resonator plate. Each of the plates has a plurality of fluid channels through which the waste or wastewater passes from one plate to the next. The top of the channel is approximately ½" in diameter and is ultimately bored down to a reduced diameter of approximately ¼".

Initially the channel is formed at approximately a 31.5 degree angle with respect to the plane of the plate and is reduced at this point from the opening diameter of ½" to ¼". Approximately one half way through the resonator plate the channel the angle of the channel is shifted to approximately 45 degrees. This angle is maintained through the exit point of the channel on the opposite side of the plate where a droplet forms, each of the droplets having a maximum width of approximately 3 mm.

Certain ones of the resonator plates are fitted with ozone distribution manifolds. For those resonator plates so fitted, each side of the plate is fitted with an ozone distribution manifold which receives ozone and sprays it through a radial, "pinwheel" configuration of channels formed radially in each manifold. This direct ozone spray acts on the waste or wastewater as it impacts on the top side of the plate and as it exits the channels on the bottom side of the plate.

The individual droplets exiting the lower side of the plate form a foam. The angles of the wastewater channels create more residence time for ozone exposure and also create turbulence and velocity for impact on the adjacent plate. The result of the absorption is a breaking of the carbon-carbon, carbon-nitrogen, and carbon-oxygen bonds. In addition, the process results in the destruction of both bacteria and viruses.

After passing through the ozone enhancement vessel, the now-treated waste or wastewater is in condition for conventional sewering into an available municipal system. With respect to the spent ozone, this material is broken down in an activated carbon filter, known as "Carulite" (trademark; Carus Corporation), for safe release into the environment.

BRIEF DESCRIPTION OF THE DRAWINGS

The present invention will be more fully understood by reference to the following detailed description of the preferred embodiments of the present invention when read in conjunction with the accompanying drawings, in which like reference characters refer to like parts throughout the views, and in which.

DETAILED DESCRIPTION OF THE PREFERRED EMBODIMENT

The drawings disclose the preferred embodiment of the present invention. While the configurations according to the illustrated embodiment are preferred, it is envisioned that alternate configurations of the present invention may be adopted without deviating from the invention as portrayed. The preferred embodiment is discussed hereafter.

Figure 1:
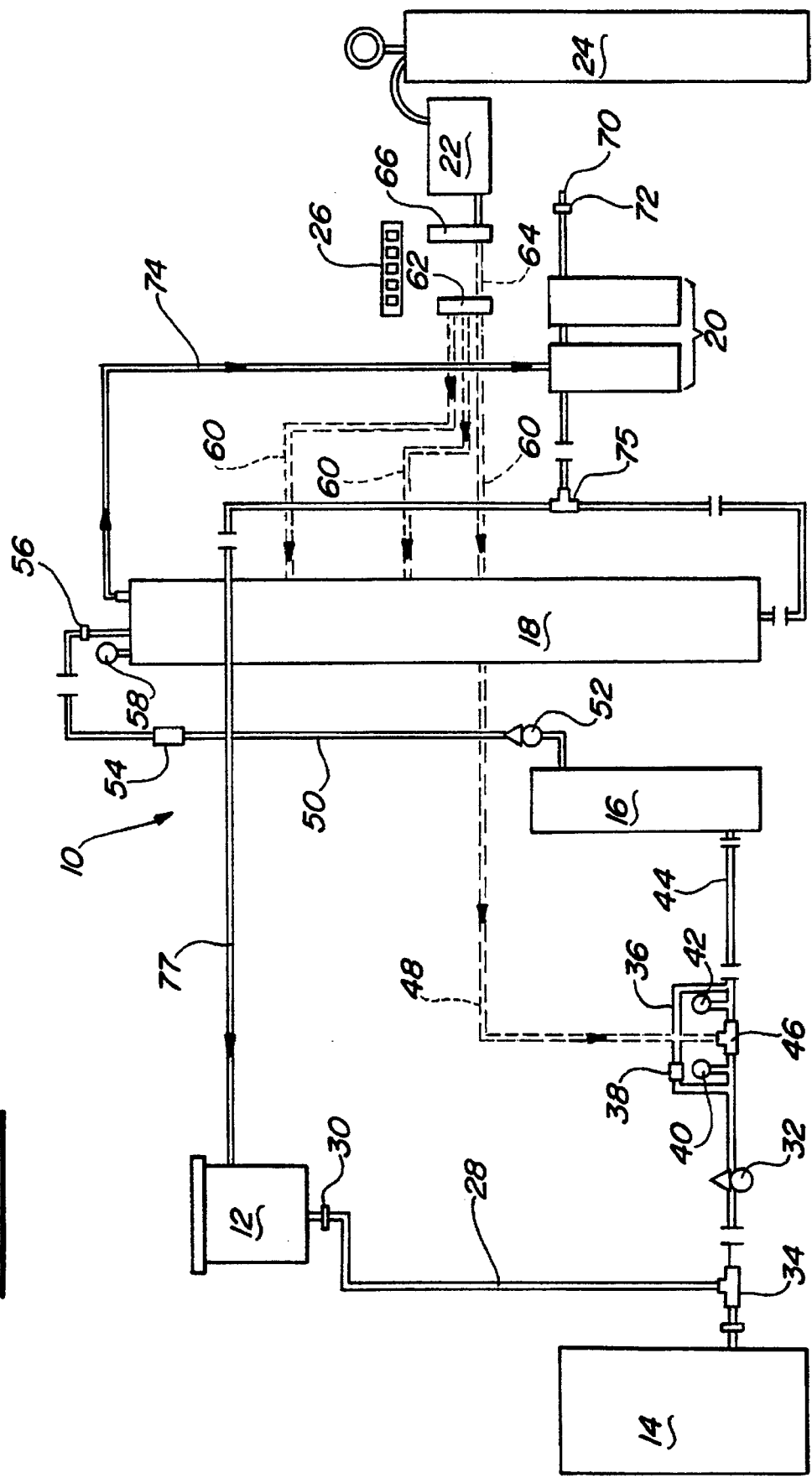
FIG. 1 is a schematic view of the system of the present invention.

FIG. 1 illustrates a schematic view of the system of the present invention, generally illustrated as 10. The system 10 includes a sample bin 12 (approximately 7 gallon capacity), a storage barrel 14 (approximately 50 gallon capacity), an ultraviolet light purifier 16 (such as the Sanitron purifier [trademark; Atlantic Ultraviolet Corporation]), an ozone enhancement vessel 18, a carbon filtration system 20 (incorporating Carulite carbon filters [trademark; Carus Corporation]), and an ozone generator 22 (such as the Model 1250 Ozone Generator produced by the Caldera Environmental Corporation, rated at 1.25 pounds per day of ozone output). The ozone is produced by feeding commercial grade oxygen (or, alternatively, clean, dry air) into the ozone generator. The generator has glass tubes lined with titanium metal. An electric current splits the oxygen molecules into two oxygen atoms. One oxygen atom then binds to other oxygen atoms to form a tri-atomic state of oxygen, or ozone.

The system 10 also includes an oxygen tank 24 (containing commercial grade oxygen), and a switch assembly 26 for controlling the several pumps of the system 10, to be described hereinafter. The system 10 further generally includes wastewater lines, denoted as solid lines, and ozone lines, denoted as broken lines.

A quantity of wastewater is poured into the sample bin 12 and enters a fluid line 28 after passing a two-way ball valve 30. A pump 32 creates a negative pressure to draw the fluid from the sample bin 12 (at approximately 10 gallons per minute). After passing a three-way ball valve 34, the sample proceeds to a venturi loop 36 having a two-way ball valve 38. A pair of pressure gauges 40 and 42 monitor the pressure of the passing fluid which thereafter enters the ultraviolet light purifier 16 by passing through a fluid line 44. The ozone acts as a catalyst with the ultraviolet light to break apart the double bonds of ketones, aldehydes, esters, and carboxylic acids. The flow rate through the purifier 16 depends on the percent transmittance of the sample, and may be adjusted so as to provide maximum ultraviolet light penetration of the sample. (For example, alcohols have a low transmittance which requires a relatively slow flow through the purifier 16. Also, darker colored fluids tend to absorb the ultraviolet light more slowly, and hence their passage through the purifier 16 must be slower.)

A quantity of ozone is also introduced into the fluid flow at this point through a "T" connection 46 that is connected to the ozone generator 22 by an ozone line 48.

After this provisional treatment, the sample may either be pumped to a holding tank (not shown) or may be directly introduced into the ozone enhancement vessel 18 via a fluid line 50. A ten gallon per minute pump 52 is fitted to the fluid line 50, as is a 0–10 gallon per minute flow rotometer (with valve) 54 and a two-way ball valve 56. The vessel 18 is pressurized to approximately 6 p.s.i. This allows for vapor oxidation of molecules. A 0–60 p.s.i. pressure gauge 58 is fitted to the generator 18 to monitor pressure within the vessel.

In addition to entering the "T" connection 46 described above, the ozone enters the vessel 18 through a series of ozone lines 60 connected to an array of air flow valves 62. The valves 62 are fluidly connected to the ozone generator 22 by a line 64 which incorporates an air flow rotometer 66.

After passing through the enhancement vessel 18, the sample passes out of the vessel through an exit line 68 through the carbon or anionic and cationic filtration system 20 and out of an outlet 70. A two-way ball valve 72 is fitted adjacent the outlet 70. Water released from the system may be introduced into municipal sewer lines (not shown).

Also fluidly connected between the vessel 18 and the filtration system 20 is an ozone "off gas" line 74 which directs spent ozone to the system 20. The activated carbon of the system 20 reduces the ozone to oxygen for safe release into the environment.

A three-way valve 75 is provided on the fluid line 68 for possible recirculation of wastewater through the system 10 via a return line 77 should additional treatment be selected.

Figure 2:
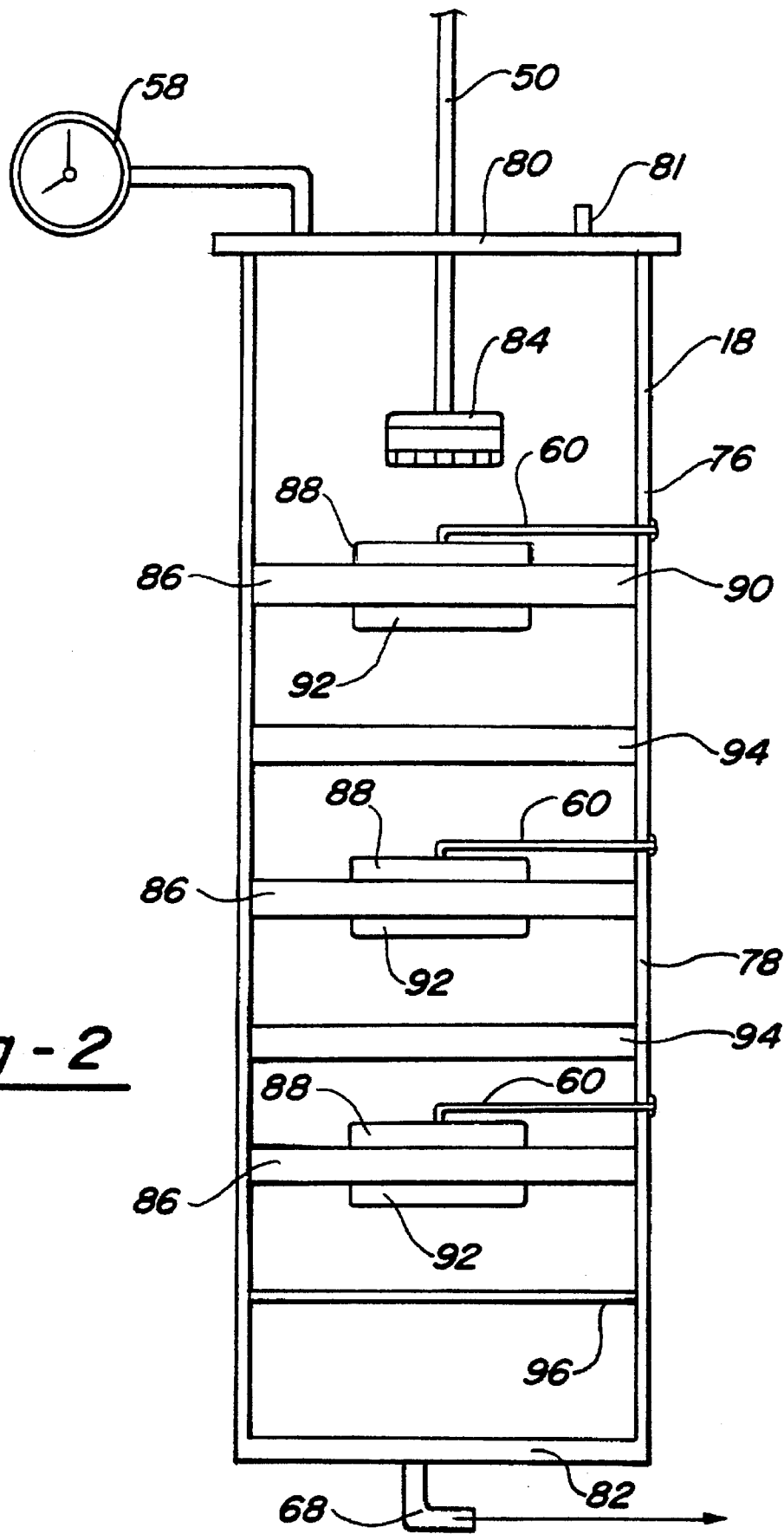
FIG. 2 is a sectional view of the ozone enhancement vessel of the present invention.

With reference to FIG. 2, a sectional view of the ozone enhancement vessel 18 is shown. The vessel 18 includes a containment shell 76 that is capable of withstanding internal pressures. The shell 76 includes a drum portion 78, a top plate 80 having a pressure relief valve 81, and a bottom plate 82. The fluid line 50 passes through the top plate 80 and terminates at an aerating nozzle 84. Wastewater is distributed by the nozzle 84 and is drawn downwardly through the combine effects of gravity and pressure.

A plurality of resonator disk assemblies 86 are fitted within the inner peripheral wall of the drum portion 78 of the shell 76 and sealingly contact the wall. Each assembly 86 includes an upper ozone distribution manifold 88, a resonator plate 90, and a lower ozone distribution manifold 92. Each of the ozone lines 60 is fluidly connected to the top side of the upper ozone distribution manifold 88 and fluidly communicates with the lower ozone distribution manifold 92. Ozone exits the manifolds 88 and 92 under pressure of approximately 20 p.s.i. as more fully detailed below with respect to FIGS. 3 and 4.

In addition to the assemblies 86, one or more resonator plates 94 may be positioned within the vessel 18 to enhance ozone absorption. These vessels are preferably not fitted with ozone distribution manifolds. As illustrated, the plates 94 may be interposed between the assemblies 86.

Still with respect to FIG. 2, one or more drip plates 94 are optionally provided within the vessel 18. The drip plates 96 include angular (not shown) which further enhance ozone absorption of the flowable waste.

The vessel 18 and its components may be composed of any of several metals, although the preferred material is stainless steel. Alternatively or additionally the components may be composed of one of several rigid plastics. The plumbing of the system 10 is preferably composed of PVC.

Figure 3:
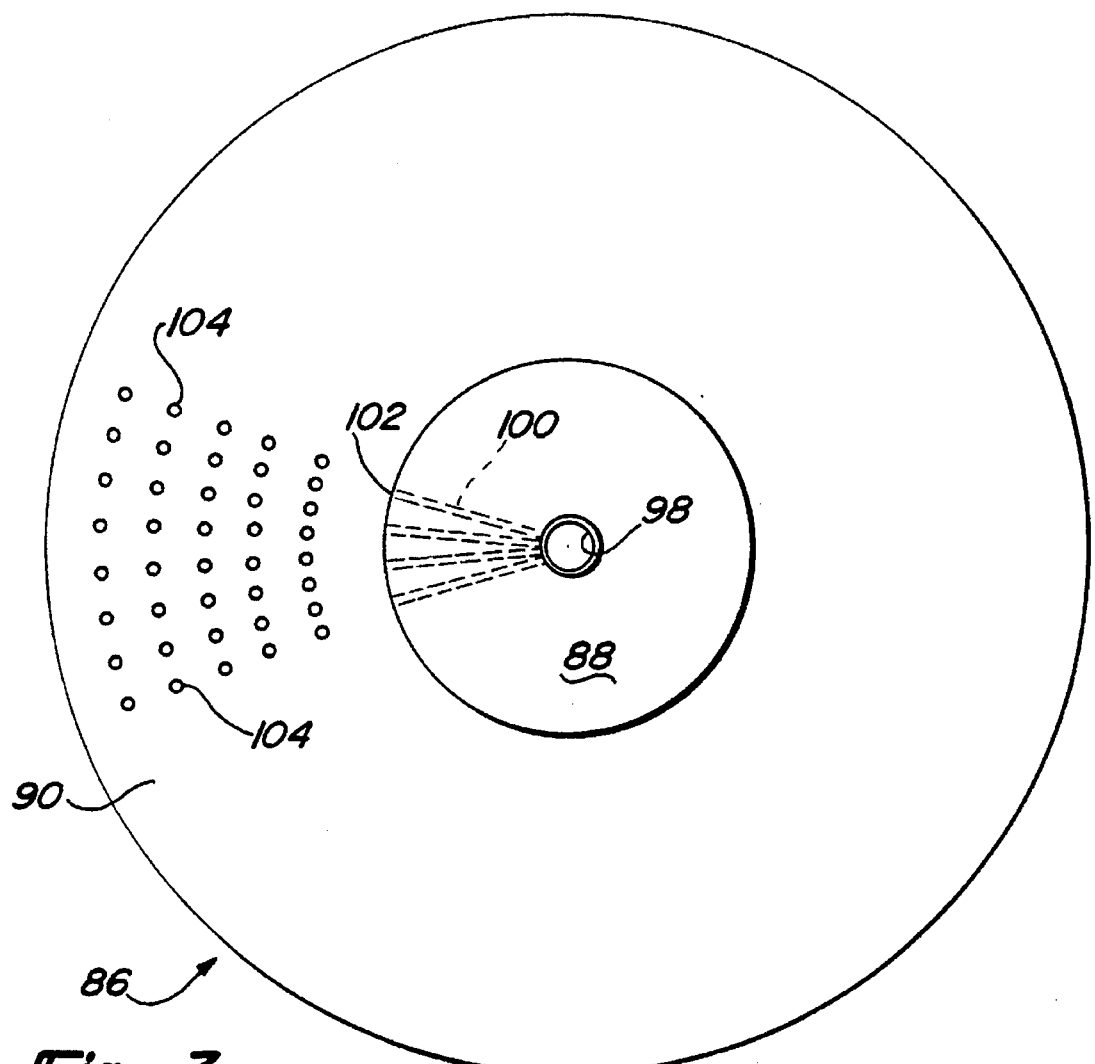
FIG. 3 is a top plan view of the resonator disk assembly of the present invention.
Figure 4:
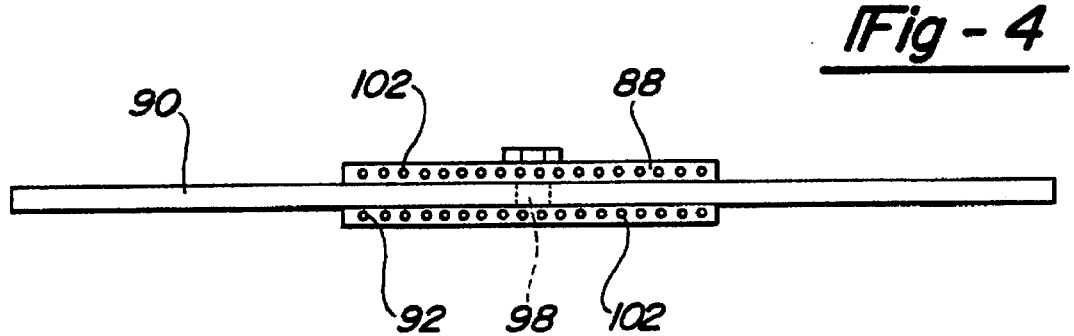
FIG. 4 is a side elevational view of the assembly of FIG. 3 and shows the ozone path between the upper and lower ozone distribution manifolds.

FIGS. 3 and 4 respectively illustrate top and side views of one of the assemblies 86. An input plenum 98 formed in the top of the upper manifold 88 for fluid connection with the ozone line 60. The plenum 98 is formed through the resonator plate 90 for fluid communication between the upper and lower manifolds 88 and 92. A plurality of radial, "pinwheel" channels 100 (shown in broken lines in FIG. 3) radiate outwardly from the plenum 98. As ozone enters the plenum 98, it is forced through these channels under pressure and outward toward openings 102 formed on the outer peripheral wall of the manifold. The openings 102 are positioned so as to allow pressurized ozone to "sweep" the upper and lower surfaces of the resonator plate 90.

A plurality of channels 104 are formed between the top and bottom sides of each of the resonator plates 90. This construction is the same whether the plates are used as part of the assembly 86 or are fitted without the upper and lower manifolds 88 and 92 as embodied by elements 94 of FIG. 2. The channels 104 allow for passage of the wastewater from the top end of the vessel 18 to the bottom end. The channels 104 are in direct line of the ozone spray emanating from the upper and lower manifolds 88 and 92.

Figure 5:
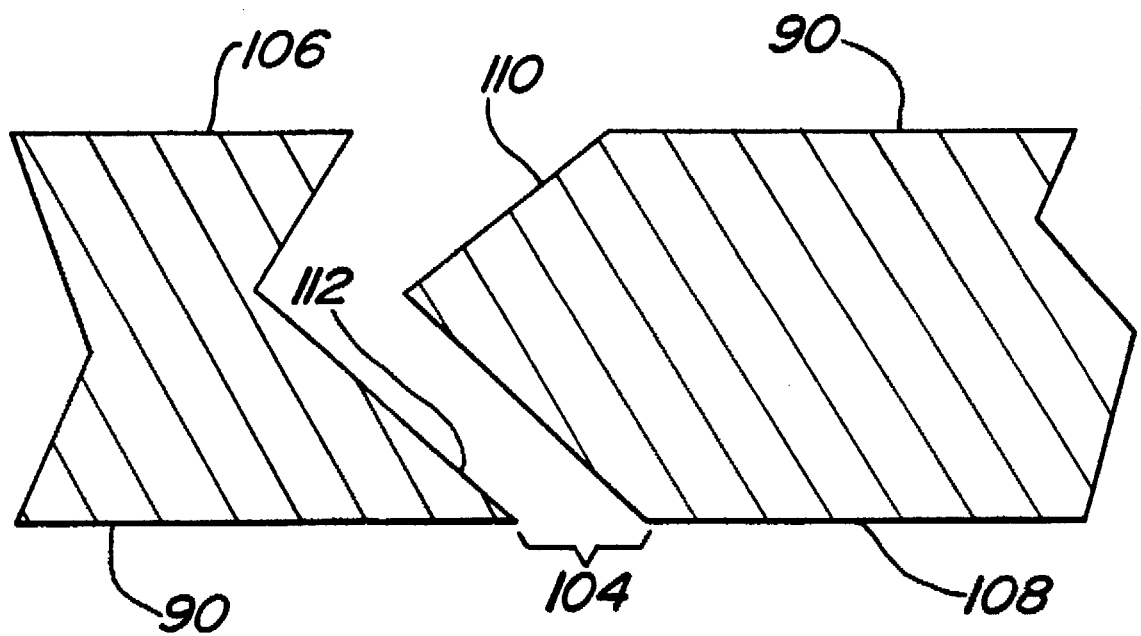
FIG. 5 is a detailed sectional view of the resonator plate of the resonator disk assembly illustrating the construction of a fluid channel.

The channels 104 are formed so as to maximize absorption of the ozone. By adjusting both the width and angle of the channels 104, maximum ozone absorption can be achieved. FIG. 5 illustrates one of the channels 104 in cross section. With respect to this figure, the channel 104 is shown between a top side 106 and a bottom side 108 of one of the plates 90. The channel 104 includes an entrance 110 and an exit 112. The entrance 110 is wider than the exit 112, the former being approximately ½" and the latter being approximately 1/16". Between the entrance 110 and the approximate midway of the plate 90, the channel 104 is severely angled, as illustrated. In addition, the entrance and exit angular configurations of the channel are preferably different, as illustrated. Preferably, although not exclusively, the entrance angle of the channel 104 is formed with its central axis being approximately 31.5 degrees with respect to the plane of the plate 90, while the exit angle of the channel 104 is formed with its central axis being approximately 45 degrees with respect to the plane of the plate 90. Of course, these angles may be adjusted as necessary to maximum ozone absorption. As noted, the angles create more residence time for ozone exposure and also create turbulence and increased velocity for impact on the next adjacent plate 90. By increasing impact between the plates, the effect is to increase ozone absorption.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

What is claimed is:

1. An ozone enhancement vessel for use in a system for the treatment of flowable waste, the system including a source of ozone, said vessel comprising:

a containment shell having an interior;

a fluid input line for introducing the flowable waste into the interior of said containment shell;

an ozone distribution manifold fitted within said interior of said shell and being fluidly connected to the source of ozone;

a resonator disk assembly fitted within said interior of said shell, said resonator disk assembly including a resonator plate, said resonator plate having a plurality of channels through which the flowable waste passes, said resonator plate having an upper side and a lower side, said ozone distribution manifold being operatively associated with at least one of said upper or said lower side of said resonator plate, each of said channels defined by a wall at least a portion of said wall being non-perpendicular with respect to one of said sides of said resonator plate; and a fluid exit line for exhausting the flowable waste from said interior of said containment shell.

2. The ozone enhancement vessel of claim 1, further including a nozzle attached to said fluid input line for distributing and aerating inflowing flowable waste.

3. The ozone enhancement vessel of claim 1, wherein said resonator plate has an upper side and a lower side and wherein said ozone distribution element comprises an ozone distribution manifold fitted to said upper side of said resonator plate, said manifold having formed therein a plurality of radial channels for the passage of ozone therethrough.

4. The ozone enhancement vessel of claim 3, further including an ozone distribution manifold fitted to said lower side of said resonator plate.

5. The ozone enhancement vessel of claim 4, wherein said ozone distribution manifolds are in fluid communication with one another.

6. The ozone enhancement vessel of claim 1, wherein each of said channels comprises an upper portion and a lower portion.

7. The ozone enhancement of claim 6, wherein said upper portion is at an angle with respect to said lower portion.

8. The ozone enhancement vessel of claim 6, wherein said upper portion defines an upper opening in said plate and said lower portion defines a lower opening in said plate, said upper opening being wider than said lower opening.

9. A method for treating flowable waste, said method comprising the steps of:

positioning a resonator disk assembly within the interior of a containment shell, said disk assembly including a resonator plate, said resonator plate having a thickness and a width and a plane define along said width;

forming a plurality of waste channels through said plate, each of said channels being defined by a wall, at least a portion of said wall being non-perpendicular with respect to said plane of said resonator plate, said resonator disk assembly further including an ozone distribution manifold connected to said resonator plate for forcing pressurized ozone into contact with the flowable waste;

introducing the flowable waste into a sample bin;

introducing the flowable waste into said containment shell;

exposing the flowable waste to ozone within said vessel and causing said flowable waste to flow through said plurality of waste channels formed in said resonator plate to slow the flow of said flowable waste therethrough such that said exposure causes absorption of at least some of said ozone by the flowable waste; and exhausting said flowable waste from said containment shell.

10. The method for treating flowable waste of claim 9 further including the step of passing the flowable waste through a first portion of one of said channels having a first angle and then through a second portion of one of said channels having a second angle, said first and second angles being different.

* * * * *